United States Patent
Kim et al.

(10) Patent No.: US 8,975,462 B2
(45) Date of Patent: *Mar. 10, 2015

(54) METHOD FOR PRODUCING HIGH-ADDED-VALUE AROMATIC PRODUCTS AND OLEFINIC PRODUCTS FROM AN AROMATIC-COMPOUND-CONTAINING OIL FRACTION

(75) Inventors: Hong Chan Kim, Jeju Special Self-Governing Province (KR); Sung Won Kim, Seoul (KR); Yong Seung Kim, Seoul (KR); Sang Hun Oh, Seoul (KR); Soo Kil Kang, Daejeon (KR); Hyuck Jae Lee, Daejeon (KR); Cheol Joong Kim, Daejeon (KR); Gyung Rok Kim, Daejeon (KR); Sun Choi, Daejeon (KR); Sam Ryong Park, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 138 days.

This patent is subject to a terminal disclaimer.

(21) Appl. No.: 13/989,161
(22) PCT Filed: Nov. 25, 2010
(86) PCT No.: PCT/KR2010/008418
§ 371 (c)(1),
(2), (4) Date: May 23, 2013
(87) PCT Pub. No.: WO2012/070706
PCT Pub. Date: May 31, 2012

(65) Prior Publication Data
US 2013/0253242 A1 Sep. 26, 2013

(51) Int. Cl.
*C07C 4/06* (2006.01)
*C10G 29/20* (2006.01)
(Continued)

(52) U.S. Cl.
CPC .............. *C07C 4/06* (2013.01); *C10G 29/205* (2013.01); *C10G 45/44* (2013.01);
(Continued)

(58) Field of Classification Search
CPC .......... C10G 1/00; C10G 1/002; C10G 1/006; C10G 1/06; C10G 35/00; C10G 35/04; C10G 45/44; C10G 45/48; C10G 45/50; C10G 55/00; C10G 55/06; C10G 57/005; C10G 69/00; C10G 69/12; C10G 69/123; C10G 2400/20; C10G 2400/30; C07C 5/00; C07C 5/10; C07C 5/11; C07C 5/22; C07C 15/00; C07C 15/02; C07C 15/04; C07C 15/06; C07C 15/08
USPC .................................. 585/253, 240, 242, 251
See application file for complete search history.

(56) References Cited

U.S. PATENT DOCUMENTS

| | | | |
|---|---|---|---|
| 4,341,914 A | 7/1982 | Berger | |
| 4,585,545 A | 4/1986 | Yancey, Jr. et al. | |

(Continued)

FOREIGN PATENT DOCUMENTS

| | | |
|---|---|---|
| CN | 101305078 A | 10/2006 |
| JP | 2007527937 A | 10/2007 |

(Continued)

OTHER PUBLICATIONS

Office Action dated May 26, 2014 for corresponding Chinese Patent Application No. 201080071134.2.
(Continued)

*Primary Examiner* — In Suk Bullock
*Assistant Examiner* — Philip Louie
(74) *Attorney, Agent, or Firm* — Abelman, Frayne & Schwab

(57) ABSTRACT

The present invention relates to a method for manufacturing aromatic products (benzene/toluene/xylene) and olefinic products from an aromatic-compound-containing oil fraction, whereby it is possible to substitute naphtha as a feedstock for aromatic production and so make stable supply and demand, and it is possible to substantially increase the yield of high-added-value olefinic and high-added-value aromatic components, by providing a method for manufacturing olefinic and aromatic products from light cycle oil comprising a hydrogen-processing reaction step, a catalytic cracking step, an separation step and a transalkylation step, and optionally also comprising a recirculation step.

13 Claims, 2 Drawing Sheets

(51) Int. Cl.
*C10G 45/44* (2006.01)
*C10G 69/04* (2006.01)
*C10G 69/12* (2006.01)
*C10G 11/05* (2006.01)
*C10G 45/48* (2006.01)
*C10G 57/00* (2006.01)
*C07C 6/12* (2006.01)

(52) U.S. Cl.
CPC .................................. *C10G 69/04* (2013.01); *C10G 69/123* (2013.01); *C10G 11/05* (2013.01); *C10G 45/48* (2013.01); *C10G 57/005* (2013.01); *C07C 6/126* (2013.01); *C10G 2400/20* (2013.01); *C10G 2400/30* (2013.01)

USPC ........... 585/323; 585/253; 585/240; 585/242; 585/251

(56) References Cited

U.S. PATENT DOCUMENTS

| | | | |
|---|---|---|---|
| 6,565,739 | B2 | 5/2003 | Winter |
| 6,867,340 | B2 | 3/2005 | Oh et al. |
| 8,778,170 | B2 | 7/2014 | Long et al. |
| 2010/0160699 | A1* | 6/2010 | Frey et al. ..................... 585/316 |
| 2011/0207979 | A1 | 8/2011 | Kim et al. |

FOREIGN PATENT DOCUMENTS

| | | |
|---|---|---|
| KR | 1020070051117 A | 5/2007 |
| WO | 2005/085391 A1 | 9/2005 |
| WO | 2007/055488 A1 | 5/2007 |
| WO | 2010/044562 A2 | 4/2010 |

OTHER PUBLICATIONS

International Search Report for PCT/KR2010/008418 Dated Aug. 24, 2011.
Office Action dated Aug. 26, 2014 for corresponding Japanese Patent Application No. 2013-540874.

\* cited by examiner

METHOD FOR PRODUCING HIGH-ADDED-VALUE AROMATIC PRODUCTS AND OLEFINIC PRODUCTS FROM AN AROMATIC-COMPOUND-CONTAINING OIL FRACTION

CROSS-REFERENCE TO RELATED APPLICATIONS

This application is a National Phase of PCT/KR2010/008418, filed 25 Nov. 2010, the disclosure of which is incorporated herein by reference.

TECHNICAL FIELD

The present invention relates to a method of producing valuable aromatic products (benzene/toluene/xylene) and olefinic products from hydrocarbonaceous oils comprising aromatic compounds

BACKGROUND ART

Globally, demand for aromatics, such as benezene, toluene and xylene, is increasing by an annual average of 4 to 6%. That is, demand for aromatic products is rapidly increasing to such a degree that the increase rate of the demand for aromatics approximates two times of the increase rate of GDP and three times of the increase rate of demand for petroleum products. Particularly, such an increase of demand is caused by the increase of demand for aromatics in China.

Conventionally, aromatic products (benzene/toluene/xylene) have been produced by hydrotreating and extracting pyrolysis gasoline produced together with main basic oil fraction products such as ethylene, propylene and the like in a naphtha cracking center using naphtha as a raw material, or by the reformate from a catalytic naphtha reforming process and separating.

However, due to the rapid increase in demand for aromatics, the supply of naphtha in the world market, including in China, have become increasingly tight since 2007. Further, conventional technologies for producing aromatic products cannot keep up with the increase in aromatic demand because they use only naphtha, which is an oil fraction having only a narrow boiling range of crude oil. Therefore, the feedstock for aromatic products, which can replace naphtha, are required.

Meanwhile, fluidized catalytic cracking (FCC) is a typical process for producing gasoline from heavy oil. Recently, a lot of FCCs has greatly been constructed.

Typical products obtained by FCC may include propylene, MTBE, alkylate, LCN (light cracked naphtha), HCN (heavy cracked naphtha), LCO (light cycle oil), SLO (slurry oil), and the like. These products are respectively used as raw materials of synthetic resins, an oxygen-containing fraction for gasoline, a high-octane fraction for gasoline, a compounding agent for gasoline, a compounding agent for diesel oil/heavy oil, a compounding agent for heavy oil, and the like.

However, all over the world, quality standards for gasoline and diesel are becoming stricter. As the regulation of the content of aromatics in diesel becomes stricter, additional treatment of the above-mentioned FCC semi-processed products is required. However, among these FCC semi-processed products, LCO (light cycle oil) includes a large amount (70% or more) of aromatic components having one or more rings, so additional treatment of LCO requires high hydrogen consumption, thereby greatly increasing utility cost.

Further, LCO is not suitable as a raw material in a conventional aromatic production process using naphtha because heavy aromatics of two or more rings must be converted into one ring aromatics, and catalyst poisoning components such as sulfur and nitrogen must be removed, although it may be possible to use LCO for producing aromatic products instead of naphtha.

However, as mentioned above, considering the rapid increase of demand for aromatics and the failure in supply of naphtha, it is expected that pressing problems in oil refining and aromatic producing industries will be simultaneously solved by inducing the production of aromatics using an oil fraction including aromatic compounds such as LCO and the like produced in the FCC process.

U.S. Pat. No. 4,585,545 discloses a method of producing high-octane gasoline containing a large amount of aromatic components using LCO (light cycle oil) obtained from FCC. However, the gasoline from this method doesn't have a high value-added product because it includes a large amount of low-value aromatics Further, this method is ineffective one as a fuel reforming technology because the issue of environmental regulation has lately attracted more considerable attention compared to the issue of an increase in octane number of gasoline.

Further, U.S. Pat. No. 6,565,739 discloses a method of producing naphtha and light olefin using LCO obtained from FCC. However, naphtha produced by this method includes a very small amount of aromatic components, because aromatic components are completely saturated in an intermediate hydrogenation process. Therefore, this method is not suitable for solving the above-mentioned problems.

DISCLOSURE

Technical Problem

Under such circumstances, the present inventors found that it is required to separate aromatic components such as benzene, toluene and xylene from various oil fractions including aromatic compounds such as LCO and the like, and it is possible to separate high value-added olefins therefrom. Based on these purposes, the present invention was devised.

An object of the present invention is to provide a novel method of producing high-concentration high value-added aromatic products using various oil fractions including LCO containing a large amount of high-aromaticity compounds as alternative raw materials to naphtha (conventional raw material of aromatic products) and obtained from FCC.

Technical Solution

In order to accomplish the above object, an aspect of the present invention provides a method of producing aromatic products and olefinic product from an aromatic compound-containing oil fraction, including the steps of: (a) hydroprocessing an aromatic compound-containing oil fraction in the presence of a catalyst to partially saturate components; (b) catalytic cracking the components partially saturated in step (a) in the presence of a cracking catalyst; (c) separating the components catalytically cracked in step (b) into (i) benzene, toluene, xylene and aromatic components of 9 or more carbon atoms, (ii) olefin components and (iii) a residual oil fraction; and (d) transalkylation of the benzene, toluene, and aromatic components of 9 or more carbon atoms separated in step (c).

In an embodiment of the present invention, in step (a) the catalyst may include at least one carrier selected from among alumina and silica, and may include at least metal selected from among group 6 metals, group 9 metals and group 10 metals.

In an embodiment of the present invention, the metal may be at least one selected from among cobalt, molybdenum, nickel and tungsten.

In an embodiment of the present invention, the aromatic compound-containing oil fraction may include 5 wt % or more of aromatics.

In an embodiment of the present invention, in step (b), the catalyst for catalytic cracking may be a spherical catalyst comprising an amorphous solid acid including silica and/or alumina or comprising a crystalline zeolite molecular sieve having a Silica/Alumina molar ratio of 300 or less and a pore size of 4~10 (Angstrom)

In an embodiment of the present invention, the catalyst for catalytic cracking may be prepared by mixing 10~95 wt % of at least one zeolite molecular sieve selected from the group consisting of faujasite (FAU), mordenite (MOR) and zeolite beta (BEA) with 5~90 wt % of an inorganic binder selected from among alumina, silica-alumina and clay and then spray drying the mixture to have a particle size of 10~300 μm.

In an embodiment of the present invention, in step (c), the residual oil fraction may include i) aromatic components of 2-ring or more, ii) 1-ring aromatic components having a hydrocarbon group of two or more carbons, and iii) 1-ring aromatic components having a naphthenic ring.

In an embodiment of the present invention, the method may further include the step of recirculating the residual oil fraction separated in step (c) to step (a).

In an embodiment of the present invention, in step (d), there may be used a catalyst comprising: a carrier including 10~95 wt % of mordenite or beta zeolite having a silca/alumina molar ratio of 20~200 and 5~90 wt % of at least one inorganic binder selected from the group consisting of gamma alumina, silica, silica-alumina, bentonite, kaolin, clinoptilolite and montmorilonite; and 0.001~0.5 parts by weight of mixed metals, as a hydrogenation metal, of platinum and a metal selected from the group consisting of tin, indium and lead, based on 100 parts by weight of the carrier, the hydrogenation metal being supported on the carrier.

In an embodiment of the present invention, the method may further include the step of recirculating the aromatic components having 11 or more carbon atoms produced in step (d) to step (b).

In an embodiment of the present invention, the method may further include the step of separating ethylene, propylene and butylene from the olefin components and then refining and productizing each of them.

In an embodiment of the present invention, the method may further include the step of separating para-xylene from mixed xylene produced by the transalkylation, after the step of transalkylation.

In an embodiment of the present invention, the method may further include the steps of: isomerizing the mixed xylene having passed through the step of separating the para-xylene; and recirculating the isomerized mixed xylene to the step of transalkylation.

In an embodiment of the present invention, the aromatic products and olefinic products may include ethylene, propylene, butylene, naphthalenes, benzene and xylene.

Advantageous Effects

According to the present invention, high-concentrated aromatic products such as benzene, toluene and xylene can be produced using an aromatic compound-containing oil fraction such as LCO from FCC instead of naphtha that is a conventional feedstock of aromatic products, thus remarkably increasing the production of aromatic products.

Particularly, among various aromatic/olefinic products, xylene (high value-added aromatic product) and propylene (high value-added olefinic product) are selectively produced, and relatively low value-added products are recovered and reprocessed to increase their values, thereby maximizing the added value of a final product.

BEST MODE

Figure 1:
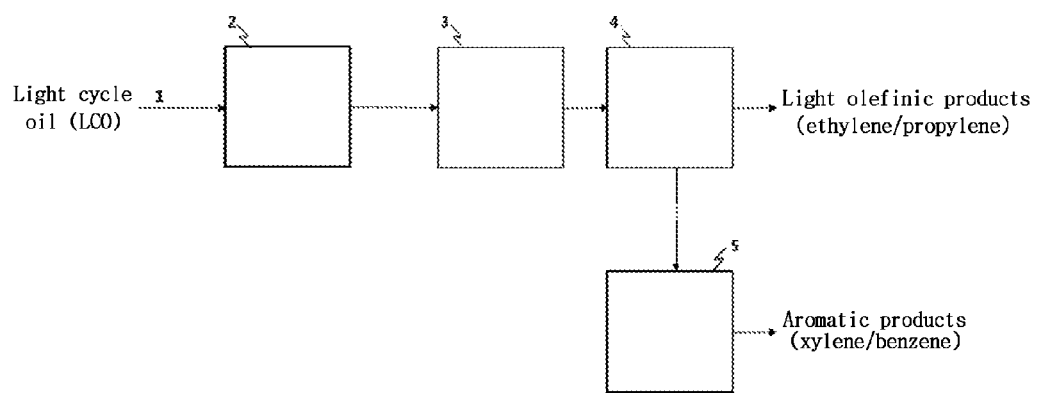
FIG. 1 is a schematic flow diagram showing a method producing aromatic products and olefinic products according to an embodiment of the present invention.

The objects, features and advantages of the present invention will be more clearly understood from the following detailed description of the preferred embodiments taken in conjunction with the accompanying drawings. Throughout the accompanying drawings, the same reference numerals are used to designate the same or similar components, and redundant descriptions thereof are omitted. Further, in the description of the present invention, when it is determined that the detailed description of the related art would obscure the gist of the present invention, the description thereof will be omitted.

The present invention provides a method of producing aromatic products and olefinic product from an aromatic compound-containing oil fraction, including the steps of: (a) hydroprocessing an aromatic compound-containing oil fraction including light cycle oil (LCO) in the presence of a catalyst to partially saturate components in the oil fraction; (b) catalytic cracking the components partially saturated in step (a) in the presence of a cracking catalyst; (c) separating the components catalytically cracked in step (b) into (i) benzene, toluene, xylene and aromatic components of 9 or more carbon atoms, (ii) olefin components and (iii) a residual oil fraction; and (d) transalkylation of the benzene, toluene, and aromatic components of 9 or more carbon atoms separated in step (c).

As the light cycle oil used as a raw material, light cycle oil produced from a fluidized catalytic cracking process is generally used, but is not limited thereto. All aromatic component-containing oil fractions produced from oil refining/petrochemical processes may be used as raw materials. The aromatic component-containing oil fraction may include 5 wt % or more of aromatic components, and preferably 15 wt % or more of aromatic components.

For example, the aromatic component-containing oil fraction may be any one selected from among raw pyrolysis gasoline (RPG), heavy raw pyrolysis gasoline (heavy RPG), treated pyrolysis gasoline (TPG), reformate, heavy aromatics, kerosene, jet oil, atmospheric gas oil, FCC gasoline, light cracked naphtha, heavy cracked naphtha, FCC decanted oil, vacuum gas oil, coker gas oil, coker diesel, coker naphtha, heavy and reduced petroleum crude oil, petroleum atmospheric distillation bottom oil, petroleum vacuum distillation bottom oil, pitch, asphalt, bitumen, tar sand oil, shale oil, liquid products derived from coal liquefaction processes, heavy hydrocarbon residues, and combinations thereof.

However, hereinafter, for convenience, embodiments of the present invention will be described based on the assumption that light cycle oil is used as a raw material. However, the scope of the present invention is not limited thereto.

FIG. 1 is a schematic flow diagram showing a method producing aromatic products and olefinic products according to an embodiment of the present invention. Referring to FIG. 1, light cycle oil (1) is introduced into a hydroprocessing step (2).

As a raw material of a fluidized catalytic cracking process for obtaining suitable light cycle oil, an oil fraction (gas oil) having a boiling point of 480 to 565 and/or an oil fraction having a boiling point of 565 or higher may be used.

Here, light cycle oil generally includes 70 to 80% of aromatic components, and is a hydrocarbon compound having a boiling point of 170 to 360. As the amount of aromatic components in light cycle oil increases, it becomes more advantageous to produce high value-added aromatic products.

In the hydroprocessing step (2), the light cycle oil is hydroprocessed in the presence of a catalyst. An aromatic mixture having two or more aromatic rings is partially saturated by the hydroprocessing. In this hydroprocessing step, aromatic components having one aromatic ring must not be saturated because they are high value-added aromatic components or can be converted into high value-added aromatic components by following steps like transalkylation process.

In the hydroprocessing step, it is preferred that all the aromatic components having two or more aromatic rings be saturated except for one aromatic ring. The reason for this is that it is not easy to decompose unnecessary aromatic rings in the subsequent steps.

The catalyst used in the hydroprocessing step may include at least one carrier selected from among alumina and silica. Further, the catalyst may include at least one metal selected from among group 6 metals, group 9 metals and group 10 metals. Preferably, the metal may be at least one selected from among cobalt, molybdenum, nickel and tungsten.

In the hydroprocessing step, denitrification and desulfurization reactions for removing impurities such as sulfur compounds, nitrogen compounds and the like from an oil fraction, as well as the partial saturation reaction of aromatic rings, occur, so impurities can be easily removed from the oil fraction without additional impurities removal processes.

The feed introduced into the hydroprocessing step, that is, light cycle oil, includes aromatics of 2 rings or more in an amount of 45 to 65 wt %. Here, 60 to 75 wt % of aromatics having 2 rings or more are mostly converted into high value-added aromatic components or 1-ring aromatic components.

The feed (3) partially saturated in the hydroprocessing step is introduced into a catalytic cracking step (4). Here, as a cracking catalyst, a shaped solid catalyst including one or more kinds of porous solid acids may be used. The solid acid may be an amorphous solid represented as silica, alumina or silica-alumina, or may be a crystalline zeolite molecular sieve having a silica/alumina molar ratio of 300 or less and a pore size of 4~10 (Angstrom).

Preferably, the crystalline zeolite molecular sieve may be used in a combination of one large-pore zeolite molecular sieve having a pore size of 6.5 or more selected from among FAU, MOR and BEA and one medium pore zeolite molecular sieve having a pore size of 5 to 6.5 selected from among MFI, MEL and FER in order that aromatic components may be reacted in pores. Here, the weight ratio of large-pore zeolite molecular sieve to medium pore zeolite molecular sieve may be 5/95 to 95/5, and preferably 50/50 to 95/5.

The catalyst for catalytic cracking may be prepared by mixing 10~95 wt % of at least one zeolite molecular sieve selected from the group consisting of faujasite (FAU), mordenite (MOR) and zeolite beta (BEA) with 5~90 wt % of an inorganic binder selected from among alumina and clay and then spray drying the mixture to have a particle size of 10~300 μm.

The catalytic cracking process using cracking catalyst serves to crack a long chain of two or more carbon atoms bonded with a 1-ring aromatic or a naphthenic ring. In the hydroprocessing step, aromatic rings of aromatic components having two or more aromatic rings, except one aromatic ring, are saturated to be converted into a naphthenic ring. In the catalytic cracking process, this naphthenic ring is cracked, thus converting the aromatic components into high value-added aromatic components or raw materials thereof.

In the catalytic cracking step, when cracking ability is excessively high, short chains having one carbon atom as well as long chains having two or more carbon atoms or a naphthenic ring are cracked, so high value-added aromatic components are converted into cheap aromatic components, and 1-ring aromatic components are converted into coke, thereby losing the values thereof. Therefore, in order for undesired portions of aromatic components not to be decomposed, cracking ability must be properly adjusted by controlling reaction temperature in the range of 349 to 749 and controlling a catalyst/oil ratio in the range of 3~15.

The amount of 1-ring aromatics of 10 or more carbon atoms in the feed introduced into the catalytic cracking step after the hydroprocessing step is about 15.7 wt %. About 66.6% of these 1-ring aromatics are decomposed in step (b) to be converted into different components. Most of the 1-ring aromatics are converted into high value-added aromatic components or raw materials thereof.

Further, about 46.3 wt % of the introduced feed is 1-ring aromatics having a naphthenic ring and about 92% of these 1-ring aromatics are converted into high value-added aromatic components or raw materials thereof.

Since aromatic rings can be lost inevitably during the catalytic cracking step, reaction conditions must be suitably adjusted in order to decrease the loss thereof.

The feed having passed through the catalytic cracking step using the cracking catalyst is introduced into a separation step (4) for separating the feed into (i) benzene, toluene, xlyene and aromatic components of 9 or more carbon atoms, (ii) olefin components and (iii) a residual oil fraction.

High value-added light olefins such as ethylene, propylene, butylene and the like are directly recovered as products in the separation step. Further, the feed having passed through the cracking step includes a large amount of naphthalenes. The naphthalenes include methyl naphthalene, dimethyl naphthalene, and the like.

Such naphthalenes, as described below, can be recirculated into the hydroprocdessing step together with residual oil fraction, or can also be separated and then additionally treated to be used for other purposes.

High value aromatic components, such as benzene, xylene and the like, and raw materials thereof, such as toluene, aromatic components of 9 or more carbon atoms and the like are sent to the following transalkylation step to be converted into high value-added aromatic components.

The residual oil fraction is separately recovered. The residual oil fraction includes, as undesired components, i) aromatic components of 2 rings or more, ii) 1-ring aromatics that cannot be converted into raw materials of high value-added aromatic products because they have a hydrocarbon group of two or more carbon atoms, iii) 1-ring aromatics that are not high value-added aromatic products and cannot be converted into raw materials of high value-added aromatic products because they have a naphthenic ring, and iv) other components that are not high value-added aromatic products and cannot be converted into raw materials of high value-added aromatic products.

The high value-added aromatic components and raw materials thereof separated in the separation step (4) are introduced into a transalkylation step (5).

In the transalkylation step (5), a disproportionation reaction of toluene, a transalkylation reaction of toluene and a C9 aromatic compound, a dealkylation reaction of alkyl aromatic compounds of C9 or more and a transalkylation reaction of benzene and aromatic compounds of C9 or more are simultaneously conducted.

Such a dealkylation reaction is an important reaction for producing toluene necessary for disportionation/transalkylation reactions. Further, such a transalkylation reaction of benzene and aromatic compounds of C9 or more is also important reaction for producing toluene and mixed xylene.

Meanwhile, it is very important to rapidly hydrogenate olefins such as ethylene, propylene and the like produced by a dealkylation reaction. When these olefins are not rapidly hydrogenated, they are re-alkylated into aromatic compounds, thus causing decreasing the conversion rate of aromatic compounds of C9 or more. Further, olefins themselves are polymerized, so the inactivation of a catalyst is caused, thereby causing accelerating the catalyst inactivation.

The catalyst used in the transalkylation step is not particularly limited, but it is preferred that a catalyst disclosed in U.S. Pat. No. 6,867,340 filed by the present applicant be used.

That is, in the transalkylation step, there may be used a catalyst including: a carrier including 10~95 wt % of mordenite or beta zeolite having a silca/alumina molar ratio of 20~200 and 5~90 wt % of at least one inorganic binder selected from the group consisting of gamma alumina, silica, silica-alumina, bentonite, kaolin, clinoptilolite and montmorilonite; and 0.001~0.5 parts by weight of mixed metals, as a hydrogenation metal, of platinum and a metal selected from the group consisting of tin, indium and lead, based on 100 parts by weight of the carrier, the hydrogenation metal being supported on the carrier. Other characteristics of the catalyst refer to the above patent document.

The high value-added aromatic components produced in the transalkylation step, that is, benzene/xylene are recovered and productized.

Figure 2:
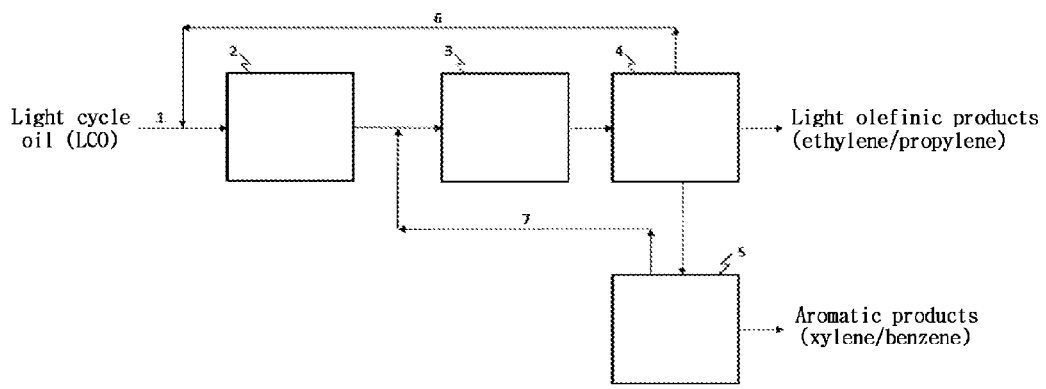
FIG. 2 is a schematic flow diagram showing a method producing aromatic products and olefinic products according to an embodiment of the present invention, the method further including a recirculation process.

FIG. 2 is a schematic flow diagram showing a method producing aromatic products and olefinic products, further including the steps of: recirculating a residual oil fraction, i.e., i) aromatic components of 2 rings or more, ii) 1-ring aromatics that cannot be converted into raw materials of high value-added aromatic products because they have a hydrocarbon group of two or more carbon atoms, iii) 1-ring aromatics that are not high value-added aromatic products and cannot be converted into raw materials of high value-added aromatic products because they have a naphthenic ring and iv) other components that are not high value-added aromatic products and cannot be converted into raw materials of high value-added aromatic products, which has been separated in the separation step (4); and recirculating the aromatic components that cannot be converted into raw materials of high value-added aromatic products after the transalkylation step (5).

Referring to FIG. 2, light cycle oil (1) is introduced into a hydroprocessing step (2), in the same manner as in FIG. 1. The light cycle oil partially saturated in the hydroprocessing step (2) passes through a catalytic cracking process (3), and is then introduced into a separation step (4) for separating the feed into (i) benzene, toluene, xylene and aromatic components of 9 or more carbon atoms, (ii) olefin components and (iii) a residual oil fraction.

The residual oil fraction (6) separated in the separation step is recirculated and mixed with the light cycle oil (1), and then introduced into the hydroprocessing step (2).

Due to this recirculation, aromatic components of 2 rings or more pass through a hydroprocessing step and a catalytic cracking step using a cracking catalyst to be decomposed into 1-ring aromatic components. Further, due to this recirculation, a hydrocarbon group having two or more carbon atoms or a naphthenic ring is converted into high value-added aromatic components or raw materials thereof.

When the recirculation step is not carried out, about 23.2 wt % of the feed introduced into the hydroprocessing step is converted into high value-added aromatic components or raw materials thereof. However, when the recirculation is carried out, about 34.5 wt % of the feed introduced into the hydroprocessing step is converted into high value-added aromatic components or raw materials thereof, thus obtaining an increase effect of about 49.2 wt %. Due to the increase in conversion rate of high value-added aromatic components or raw materials thereof, the yield of final high value-added aromatic products can be increased by about 38 wt %.

That is, the production of aromatic products according to the method of the present invention can be maximized by the introduction of the recirculation step. Therefore, it is preferred that this recirculation step be additionally performed, but the present invention is not limited thereto.

Figure 3:
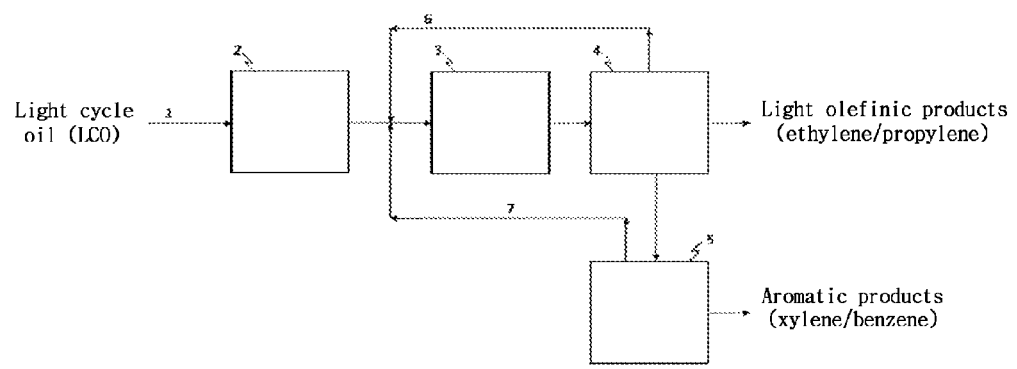
FIG. 3 is a schematic flow diagram showing a method producing aromatic products and olefinic products according to an embodiment of the present invention, the method further including a recirculation process.

FIG. 3 is a schematic flow diagram showing a method producing aromatic products and olefinic products according to an embodiment of the present invention, further including another recirculation step.

As shown in FIG. 3, the residual oil fraction (6) is recirculated and mixed with the partially-saturated feed introduced into the catalytic cracking step (3), and then introduced into the catalytic cracking step (3).

Due to this recirculation, the naphthenic ring or a hydrocarbon group of two or more carbon atoms of the 1-ring aromatic components having a naphthenic ring or a hydrocarbon group of two or more carbon atoms, which is present in the residual oil fraction (6), is decomposed and converted into high value-added aromatic components or raw materials thereof during the catalytic cracking step.

Further, among the components separated in the separation step (4), benzene, toluene, xylene and components of 9 or more carbon atoms are introduced into a transalkylation step (5).

After the transalkylation step (5), aromatic components of 11 or more carbon atoms that cannot be converted into raw material of high value-added aromatic components may be recovered and then recirculated and introduced into the catalytic cracking step (3) using the cracking catalyst. That is, aromatic components of 11 or more carbon atoms are mixed with the light cycle oil partially saturated by the hydroprocessing step, and then introduced into the catalytic cracking step (3) using the cracking catalyst.

The components that cannot be converted into raw material of high value-added aromatic components produced in the transalkylation step or inevitably introduced into the transalkylation step from the separation step, that is, i) aromatic components of 2 rings or more, ii) 1-ring aromatics that cannot be converted into raw materials of high value-added aromatic products because they have a hydrocarbon group of two or more carbon atoms, iii) 1-ring aromatics that are not high value-added aromatic products and cannot be converted into raw materials of high value-added aromatic products because they have a naphthenic ring and iv) other components that are not high value-added aromatic products and cannot be converted into raw materials of high value-added aromatic products are required to be re-decomposed.

Therefore, in order to re-decompose the above components, these components can be recirculated into the catalytic cracking step (3) using the cracking catalyst. Due to this recirculation step, it is possible to prevent unnecessary components from being accumulated in the transalkylation step and to convert the components that cannot be converted into raw material of high value-added aromatic components into high value-added aromatic components, thus increasing the yield of high value-added aromatics. The effects due to the recirculation are described in more detail in the following embodiment.

In an embodiment, the yield of benzene and xylene, which are high value-added aromatic components, is increased due to the recirculation.

Figure 4:
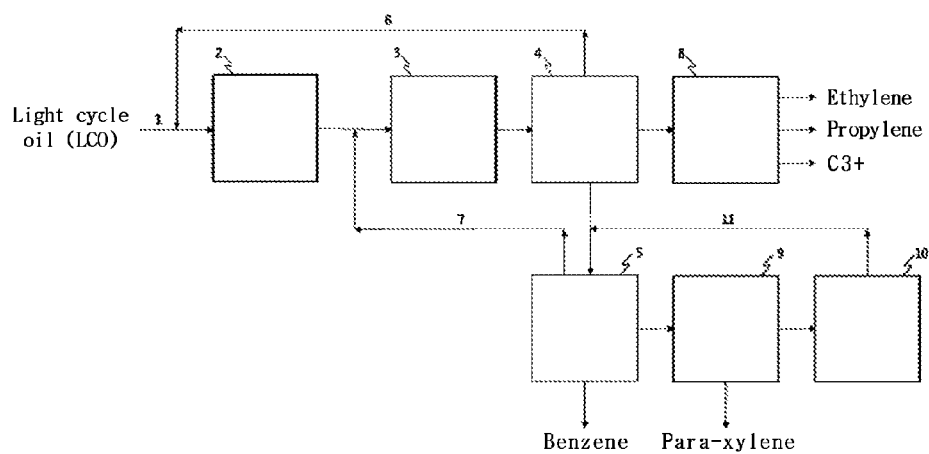
FIG. 4 is a schematic flow diagram showing a method producing aromatic products and olefinic products according to an embodiment of the present invention, the method further including the steps of: separating and refining ethylene propylene and butylene; separating para-xylene; and isomerizing xylene.

FIG. 4 is a schematic flow diagram showing a method producing aromatic products and olefinic products according to an embodiment of the present invention. As shown in FIG. 4, the method may further include the step (8) of: respectively separating and refining ethylene, propylene and butylene and then productizing each of them at the rear end of a main separation column.

Further, the method may further include the step (9) of separating para-xylene from the mixed xylene produced in the transalkylation step (5). Conventional techniques like adsorption or crystallization can used to separate para-xylene.

Since para-xylene is high value-added compared to ortho-xylene or meta-xylene, it is advantageous to separate and obtain only para-xylene.

Ortho-xylene and mixed xylene, except para-xylene, may be introduced into a xylene isomerization step (10). Para-xylene, meta-xylene and ortho-xylene of mixed xylene produced in the transalkylation step (5) form a equilibrium mixture of xylene isomers. Here, since only para-xylene has been separated from mixed xylene in the separation step, when the mixed xylene, from which para-xylene was separated, forms a equilibrium mixture again, high economic value-added para-xylene can be additionally added.

In this process, benzene and toluene are produced, and these compounds (II) are recirculated into a transalkylation step. In the transalkylation step, the recirculated benzene and toluene can be converted into xylene. Consequently, all fractions discharged from the xylene isomerization step are recirculated into the transalkylation step, and thus para-xylene can be additionally obtained.

That is, when the para-xylene separation step and the xylene isomerization step were not added, only mixed xylene was produced. However, when these steps are added, meta-xylene and ortho-xylene are not produced, and only high value-added para-xylene can be obtained.

MODE FOR INVENTION

Hereinafter, the present invention will be described in more detail with reference to the following Examples. However, these Examples are set forth to illustrate the present invention, and the scope of the present invention is not limited thereto.

Example 1

As the light cycle oil used in the method of present invention, as shown in Table 1 below, light cycle oil, which is an oil fraction produced by a fluidized catalytic cracking process and having a boiling point range of 170 to 360, was provided.

TABLE 1

|  | Feed |
|---|---|
| Paraffin + Olefin | 4.680 |
| Ethylene | — |
| Propylene | — |
| Butylene | — |
| Naphthene | 0.502 |
| Total amount of aromatics | 84.121 |
| 1-ring aromatics | 39.024 |
| 1-ring aromatics not having naphthenic ring | 26.951 |
| BTX + C9 | 9.431 |
| B + X | 1.473 |
| T + C9 | 7.958 |
| B | 0.024 |
| T | 0.344 |
| X | 1.449 |
| C9 | 7.614 |
| 1-ring aromatics having one naphthenic ring | 12.072 |
| 1-ring aromatics having two naphthenic rings | — |
| 2-ring aromatics | 40.975 |
| 2-ring aromatics not having naphthenic ring | 38.398 |
| 2-ring aromatics having one naphthenic ring | 2.577 |
| 2-ring aromatics having two naphthenic rings | — |
| 3-ring aromatics | 4.123 |
| Others | 10.697 |

In Example 1, since feed is light cycle oil of FCC process, the physical properties, composition and yield of the oil fraction may be changed depending on the kind of raw material used and the operation conditions of the fluidized catalytic cracking process.

The raw feed was introduced into a hydroprocessing step. The hydroprocessing was performed in a fixed-bed reactor using a nickel-molybdenum-combined catalyst. The reaction conditions of the hydroprocessing step are shown in Table 2 below.

TABLE 2

| Kind of catalyst and amount<br>Operation conditions | $NiMo/Al_2O_3$/75 cc |
|---|---|
| Pressure, kg/cm$^2$ | 60 |
| Gas/Oil, Nm$^3$/kl | 500 |
| LHSV, hr$^{-1}$ | 1.5 |
| Temperature, | 300 |

The consumption of hydrogen in the hydroprocessing step was 1.186 based on feed 100 weight.

The compositions before and after the hydroprocessing are shown in Table 3 below.

TABLE 3

|  | Feed | After hydroprocessing |
|---|---|---|
| $H_2$ consumption |  | 1.186 |
| Coke | — | — |
| $H_2S$ |  | 0.417 |
| $H_2$ |  | — |
| Paraffin + Olefin | 4.680 | 5.376 |
| Ethylene | — | — |
| Propylene | — | — |
| Butylene | — | — |
| Naphthene | 0.502 | 1.744 |
| Total amount of aromatics | 84.121 | 80.020 |
| 1-ring aromatics | 39.024 | 71.331 |
| 1-ring aromatics not having naphthenic ring | 26.951 | 27.281 |
| BTX + C9 | 9.431 | 5.904 |
| B + X | 1.473 | 0.723 |
| T + C9 | 7.958 | 5.180 |
| B | 0.024 | — |
| T | 0.344 | 0.097 |
| X | 1.449 | 0.723 |
| C9 | 7.614 | 5.084 |
| 1-ring aromatics having one naphthenic ring | 12.072 | 39.892 |
| 1-ring aromatics having two naphthenic rings | — | 4.157 |
| 2-ring aromatics | 40.975 | 8.027 |
| 2-ring aromatics not having naphthenic ring | 38.398 | 4.295 |
| 2-ring aromatics having one naphthenic ring | 2.577 | 3.599 |
| 2-ring aromatics having two naphthenic rings | — | 0.134 |
| 3-ring aromatics | 4.123 | 0.662 |
| Others | 10.697 | 13.630 |

As shown in Table 3 above, it can be ascertained that aromatic components of 2 rings or more existed in large amounts, rapidly decreases after the hydroprocessing. Further, it can be ascertained that 1-ring aromatic components increases about two times after the hydroprocessing, and that, among the 1-ring aromatic components, 1-ring aromatic components having a naphthenic ring increase from about 12 wt % to 40 wt % after the hydroprocessing. The 1-ring aromatic components having a naphthenic ring would be converted into high value-added aromatic components or raw material thereof because their naphthenic rings are cracked during a fluidized catalytic cracking reaction.

The feed produced by the hydroprocessing was introduced into a fluidized catalytic cracking reactor. Here, a commercially available silica-alumina catalyst containing Y-type zeolite (the catalyst including 49% of alumina, 33% of silica, 2% of rare earth and a residue of inorganic binder) was used. Further, reaction temperature was 549, reaction pressure was 25.3 psig, a catalyst/oil ratio is 8, and WHSV was 27.2 $hr^{-1}$. Further, the fluidized catalytic cracking reaction of the feed was performed using a catalyst circulation fluidized-bed reactor capable of continuously regenerating an inactivated catalyst.

The results of comparing the feed compositions before and after the fluidized catalytic cracking reaction are shown in Table 4 below.

TABLE 4

|  | Feed | Hydroprocessing | Fluidized catalytic cracking |
|---|---|---|---|
| $H_2$ consumption |  | 1.186 | — |
| Coke | — | — | 11.027 |
| $H_2S$ |  | 0.417 | 0.420 |
| $H_2$ |  | — | 0.065 |
| Paraffin + Olefin | 4.680 | 5.376 | 24.745 |
| Ethylene | — | — | 1.766 |
| Propylene | — | — | 4.119 |
| Butylene | — | — | 2.124 |
| Naphthene | 0.502 | 1.744 | 0.493 |
| Total amount of aromatics | 84.121 | 80.020 | 56.661 |
| 1-ring aromatics | 39.024 | 71.331 | 28.561 |
| 1-ring aromatics not having naphthenic ring | 26.951 | 27.281 | 25.404 |
| BTX + C9 | 9.431 | 5.904 | 18.428 |
| B + X | 1.473 | 0.723 | 6.941 |
| T + C9 | 7.958 | 5.180 | 11.487 |
| B | 0.024 | — | 0.686 |
| T | 0.344 | 0.097 | 3.557 |
| X | 1.449 | 0.723 | 6.255 |
| C9 | 7.614 | 5.084 | 7.930 |
| 1-ring aromatics having one naphthenic ring | 12.072 | 39.892 | 3.157 |
| 1-ring aromatics having two naphthenic rings | — | 4.157 | — |
| 2-ring aromatics | 40.975 | 8.027 | 25.123 |
| 2-ring aromatics not having naphthenic ring | 38.398 | 4.295 | 23.590 |
| 2-ring aromatics having one naphthenic ring | 2.577 | 3.599 | 1.533 |
| 2-ring aromatics having two naphthenic rings | — | 0.134 | — |
| 3-ring aromatics | 4.123 | 0.662 | 2.977 |
| Others | 10.697 | 13.630 | 1.890 |

As shown in Table 4 above, it can be ascertained that the amount of benzene/xylene, which are high value-added aromatic components, was increased by 859.9% compared to that of the initial feed. Further, it can be ascertained that the amount of toluene and C9, which would be converted into raw materials of benzene/xylene by transalkylation, is increased by about 121.7% compared to that of the initial feed.

Comparing the feed (that is, the feed after the hydroprocessing) before and after the fluidized catalytic cracking reaction, it can be ascertained that the amount of benzene/xylene, which are high value-added aromatic components, was increased by 95.4%. Further, it can be ascertained that the amount of toluene and C9, which would be converted into raw materials of benzene/xylene by transalkylation, was increased by about 371.2%.

Here, additionally, light olefins, which were not contained in the introduced feed, were produced. Specifically, ethylene was produced in an amount of 1.766, propylene was 4.119, and butylene was 2.124.

Among the components produced by the fluidized catalytic cracking reaction, the light olefins are recovered, and other components are introduced into a transalkylation step.

The results of comparing the yields before and after transalkylation are shown in Table 5 below.

TABLE 5

|  | Feed | Hydroprocessing | Fluidized catalytic cracking | Transalkylation |
|---|---|---|---|---|
| $H_2$ consumption |  | 1.186 | — | 0.224 |
| Coke | — | — | 11.027 | 11.027 |
| $H_2S$ |  | 0.417 | 0.420 | 0.420 |
| $H_2$ |  | — | 0.065 | 0.065 |
| Paraffin + Olefin | 4.680 | 5.376 | 24.745 | 27.575 |

TABLE 5-continued

|  | Feed | Hydro-processing | Fluidized catalytic cracking | Transalkylation |
|---|---|---|---|---|
| Ethylene | — | — | 1.766 | 1.766 |
| Propylene | — | — | 4.119 | 4.119 |
| Butylene | — | — | 2.124 | 2.124 |
| Naphthene | 0.502 | 1.744 | 0.493 | 0.179 |
| Total amount of aromatics | 84.121 | 80.020 | 56.661 | 54.360 |
| 1-ring aromatics | 39.024 | 71.331 | 28.561 | 26.260 |
| 1-ring aromatics not having naphthenic ring | 26.951 | 27.281 | 25.404 | 24.031 |
| BTX + C9 | 9.431 | 5.904 | 18.428 | 20.070 |
| B + X | 1.473 | 0.723 | 6.941 | 20.070 |
| T + C9 | 7.958 | 5.180 | 11.487 | — |
| B | 0.024 | — | 0.686 | 2.649 |
| T | 0.344 | 0.097 | 3.557 | — |
| X | 1.449 | 0.723 | 6.255 | 17.421 |
| C9 | 7.614 | 5.084 | 7.930 | — |
| 1-ring aromatics having one naphthenic ring | 12.072 | 39.892 | 3.157 | 2.228 |
| 1-ring aromatics having two naphthenic rings | — | 4.157 | — | — |
| 2-ring aromatics | 40.975 | 8.027 | 25.123 | 25.123 |
| 2-ring aromatics not having naphthenic ring | 38.398 | 4.295 | 23.590 | 23.590 |
| 2-ring aromatics having one naphthenic ring | 2.577 | 3.599 | 1.533 | 1.533 |
| 2-ring aromatics having two naphthenic rings | — | 0.134 | — | — |
| 3-ring aromatics | 4.123 | 0.662 | 2.977 | 2.977 |
| Others | 10.697 | 13.630 | 1.890 | 1.890 |

As shown in Table 5 above, it can be ascertained that, after the transalkylation, benzene was increased by 285.5%, and xylene, is increased by 178.5%, compared to the transalkylation feed. Further, it can be ascertained that, after the transalkylation, the sum of benzene and xylene was increased by about 189.1%.

Since the transalkylation is not a decomposition process, the amount of olefins was not additionally increased.

Example 2

Example 2 was carried out using the same feed and reaction conditions as in Example 1.

Further, Example 2 was carried out in the same manner as in Example 1, except that i) aromatic components of 2 rings or more, ii) 1-ring aromatics that cannot be converted into raw materials of high value-added aromatic products because they have a hydrocarbon group of two or more carbon atoms, iii) 1-ring aromatics that are not high value-added aromatic products and cannot be converted into raw materials of high value-added aromatic products because they have a naphthenic ring and iv) other components that are not high value-added aromatic products and cannot be converted into raw materials of high value-added aromatic products, the components i), ii), iii) and iv) having been produced by the fluidized catalytic cracking step after the hydroprocessing step, were recirculated such that these components i), ii), iii) and iv) were mixed with the light cycle oil introduced into the hydroprocessing step.

The compositions of light cycle oil, Example 1 and Example 2 used as raw materials are shown in Table 6 below.

TABLE 6

|  | Feed | Example 1 | Example 2 |
|---|---|---|---|
| $H_2$ consumption |  | 1.410 | 2.159 |
| Coke |  | 11.027 | 18.806 |
| $H_2S$ |  | 0.420 | 0.420 |
| $H_2$ |  | 0.065 | 0.110 |
| Paraffin + Olefin | 4.680 | 27.575 | 39.791 |
| Ethylene | — | 1.766 | 2.852 |
| Propylene | — | 4.119 | 6.840 |
| Butylene | — | 2.124 | 2.556 |
| Naphthene | 0.502 | 0.179 | 0.296 |
| Total amount of aromatics | 84.121 | 54.360 | 33.044 |
| 1-ring aromatics | 39.024 | 26.260 | 33.044 |
| 1-ring aromatics not having naphthenic ring | 26.951 | 24.031 | 33.044 |
| BTX + C9 | 9.431 | 20.070 |  |
| B + X | 1.473 | 20.070 |  |
| T + C9 | 7.958 | — |  |
| B | 0.024 | 2.649 | 4.209 |
| T | 0.344 | — | — |
| X | 1.449 | 17.421 | 25.978 |
| C9 | 7.614 |  |  |
| 1-ring aromatics having one naphthenic ring | 12.072 | 2.228 | — |
| 1-ring aromatics having two naphthenic rings | — | — | — |
| 2-ring aromatics | 40.975 | 25.123 | — |
| 2-ring aromatics not having naphthenic ring | 38.398 | 23.590 | — |
| 2-ring aromatics having one naphthenic ring | 2.577 | 1.533 | — |
| 2-ring aromatics having two naphthenic rings | — | — | — |
| 3-ring aromatics | 4.123 | 2.977 | — |
| Others | 10.697 | 1.890 | — |

As shown in Table 6 above, it can be ascertained that, in Example 2, the recirculation step was additionally performed, so aromatic components of 2 rings or more were scarcely included, and the yield of olefins such as ethylene, propylene, butylene and the like was greatly increased. Further, it can be ascertained that the yield of aromatics such as benzene and xylene was also greatly increased compared to that of Example 1 in which the recirculation step was not included.

Consequently, there is an advantage in that high value-added aromatics and olefins can be obtained in a high yield by the recirculation step.

Example 3

Example 3 was carried out using the same raw materials and reaction conditions as in Example 1.

Further, Example 3 was carried out in the same manner as in Example 1, except that a step of recirculating i) aromatic components of 2 rings or more, ii) 1-ring aromatics that cannot be converted into raw materials of high value-added aromatic products because they have a hydrocarbon group of two or more carbon atoms, iii) 1-ring aromatics that are not high value-added aromatic products and cannot be converted into raw materials of high value-added aromatic products because they have a naphthenic ring and iv) other components that are not high value-added aromatic products and cannot be converted into raw materials of high value-added aromatic products, the components i), ii), iii) and iv) having been produced by the fluidized catalytic cracking process after the hydroprocessing step, and thus mixing the components i), ii), iii) and iv) with the light cycle oil introduced into the hydroprocessing step; and a step of recirculating the components having passed through the transalkylation step and required to be re-decomposed, and thus mixing these components with the partially-saturated light cycle oil introduced into the fluidized catalytic cracking process were additionally performed.

The compositions of light cycle oil, Example 1, Example 2 and Example 3 used as raw materials are shown in Table 7 below.

TABLE 7

|  | Feed | Example 1 | Example 2 | Example 3 |
|---|---|---|---|---|
| $H_2$ consumption |  | 1.410 | 2.159 | 2.163 |
| Coke |  | 11.027 | 18.806 | 18.806 |
| $H_2S$ |  | 0.420 | 0.420 | 0.420 |
| $H_2$ |  | 0.065 | 0.110 | 0.110 |
| Paraffin + Olefin | 4.680 | 27.575 | 39.791 | 39.855 |
| Ethylene | — | 1.766 | 2.852 | 2.852 |
| Propylene | — | 4.119 | 6.840 | 6.840 |
| Butylene | — | 2.124 | 2.556 | 2.556 |
| Naphthene | 0.502 | 0.179 | 0.296 | 0.296 |
| Total amount of aromatics | 84.121 | 54.360 | 33.044 | 32.981 |
| 1-ring aromatics | 39.024 | 26.260 | 33.044 | 32.981 |
| 1-ring aromatics not having naphthenic ring | 26.951 | 24.031 | 33.044 | 32.981 |
| BTX + C9 | 9.431 | 20.070 | 30.187 | 30.366 |
| B + X | 1.473 | 20.070 | 30.187 | 30.366 |
| T + C9 | 7.958 | — | — | — |
| B | 0.024 | 2.649 | 4.209 | 4.217 |
| T | 0.344 | — | — | — |
| X | 1.449 | 17.421 | 25.978 | 26.148 |
| C9 | 7.614 | — | — | — |
| 1-ring aromatics having one naphthenic ring | 12.072 | 2.228 | — | — |
| 1-ring aromatics having two naphthenic rings | — | — | — | — |
| 2-ring aromatics | 40.975 | 25.123 | — | — |
| 2-ring aromatics not having naphthenic ring | 38.398 | 23.590 | — | — |
| 2-ring aromatics having one naphthenic ring | 2.577 | 1.533 | — | — |
| 2-ring aromatics having two naphthenic rings | — | — | — | — |
| 3-ring aromatics | 4.123 | 2.977 | — | — |
| Others | 10.697 | 1.890 | — | — |

As shown in Table 7 above, it can be ascertained that, since the two recirculation steps were additionally performed in Example 3, the amount of ethylene was increased by 61.5%, the amount of propylene was increased by 57.3% and the amount of butylene was increased by 20.3%, compared to those of Example 1. Further, it can be ascertained that, in Example 3, the amounts of benzene and xylene, which are high value-added aromatic components, were greatly increased by about 159% and about 150%, respectively.

Comparative Example 1

In Comparative Example 1, the same feed as in Example 1 was used, and this feed was passed through a hydroprocessing step, a fluidized catalytic cracking step and a separation step.

Here, the conditions applied to each of the steps were the same as those of Example 1.

Comparative Example 2

Comparative Example 2 was carried out in the same manner as in Comparative Example 1, except that, in the separation step, i) aromatic components of 2 rings or more, ii) 1-ring aromatics that cannot be converted into raw materials of high value-added aromatic products because they have a hydrocarbon group of two or more carbon atoms, iii) 1-ring aromatics that are not high value-added aromatic products and cannot be converted into raw materials of high value-added aromatic products because they have a naphthenic ring and iv) other components that are not high value-added aromatic products and cannot be converted into raw materials of high value-added aromatic products were recirculated into the hydroprocessing step.

The results of comparing Comparative Examples 1 and 2 with Examples 1 to 3 are shown in Table 8 below.

TABLE 8

|  | Feed | Example 1 | Example 2 | Example 3 | Comp. Example 1 | Comp. Example 2 |
|---|---|---|---|---|---|---|
| $H_2$ consumption |  | 1.410 | 2.159 | 2.163 | 1.186 | 1.830 |
| Coke |  | 11.027 | 18.806 | 18.806 | 11.076 | 18.806 |
| $H_2S$ |  | 0.420 | 0.420 | 0.420 | 0.004 | 0.420 |
| $H_2$ |  | 0.065 | 0.110 | 0.110 | 0.066 | 0.110 |
| Paraffin + Olefin | 4.680 | 27.575 | 39.791 | 39.855 | 24.824 | 35.573 |
| Ethylene | — | 1.766 | 2.852 | 2.852 | 1.773 | 2.852 |
| Propylene | — | 4.119 | 6.840 | 6.840 | 4.137 | 6.840 |
| Butylene | — | 2.124 | 2.556 | 2.556 | 2.134 | 2.556 |
| Naphthene | 0.502 | 0.179 | 0.296 | 0.296 | 0.495 | 0.841 |
| Total amount of aromatics | 84.121 | 54.360 | 33.044 | 32.981 | 56.913 | 36.387 |
| 1-ring aromatics | 39.024 | 26.260 | 33.044 | 32.981 | 28.688 | 36.387 |
| 1-ring aromatics not having naphthenic ring | 26.951 | 24.031 | 33.044 | 32.981 | 25.517 | 34.755 |
| BTX + C9 | 0.024 | 20.070 | 30.187 | 30.366 | 18.510 | 27.908 |
| B + X | 0.344 | 20.070 | 30.187 | 30.366 | 6.972 | 10.768 |
| T + C9 | 1.449 | — | — | — | 11.538 | 17.140 |
| B | 12.072 | 2.649 | 4.209 | 4.217 | 0.689 | 1.164 |
| T | — | — | — | — | 3.573 | 6.116 |
| X | 40.975 | 17.421 | 25.978 | 26.148 | 6.282 | 9.604 |
| C9 | 38.398 | — | — | — | 7.966 | 11.024 |
| 1-ring aromatics having one naphthenic ring | 2.577 | 2.228 | — | — | 3.171 | 1.632 |
| 1-ring aromatics having two naphthenic rings | — | — | — | — | — | — |
| 2-ring aromatics | 4.123 | 25.123 | — | — | 25.234 | — |
| 2-ring aromatics not having naphthenic ring | 10.697 | 23.590 | — | — | 23.695 | — |
| 2-ring aromatics having one naphthenic ring |  | 1.533 | — | — | 1.539 | — |

TABLE 8-continued

|  | Feed | Example 1 | Example 2 | Example 3 | Comp. Example 1 | Comp. Example 2 |
|---|---|---|---|---|---|---|
| 2-ring aromatics having two naphthenic rings |  | — | — | — | — | — |
| 3-ring aromatics |  | 2.977 | — | — | 2.991 | — |
| Others |  | 1.890 | — | — | 1.898 | — |

As shown in Table 8 above, it can be ascertained that the yields of benzene and xylene of Examples 1 to 3 in each which light cycle oil was treated according to the present invention were greatly increased compared to those of Comparative Examples 1 and 2.

Particularly, it can be ascertained that, in the case of Example 3 including the two recirculation steps, aromatic components of 2 rings or more scarcely existed, and that the yields of high value-added olefins and high value-added aromatics of Example 3 were greatly high compared to those of Comparative Examples 1 and 2.

Although the embodiments of the present invention have been disclosed for illustrative purposes, it will be appreciated that the present invention is not limited thereto, and those skilled in the art will appreciate that various modifications, additions and substitutions are possible, without departing from the scope and spirit of the invention. Accordingly, any and all modifications, variations or equivalent arrangements should be considered to be within the scope of the invention, and the detailed scope of the invention will be disclosed by the accompanying claims.

The invention claimed is:

1. A method of producing aromatics and olefins from an oil fraction comprising aromatic compounds, comprising:
    a) hydroprocessing the oil fraction comprising aromatic compounds in the presence of a hydroprocessing catalyst to partially saturate aromatic components having two or more aromatic rings into aromatic components having one aromatic ring, such that an amount of aromatic components having one aromatic ring in the oil fraction is increased;
    b) catalytic catalytically cracking the hydroprocessed oil fraction from step (a) in the presence of a cracking catalyst;
    c) separating the cracked hydroprocessed oil fraction from step (b) into
        i. benzene, toluene, xylene and aromatic components of 9 or more carbon atoms,
        ii. olefin components, and
        iii. a residual oil fraction comprising (I) aromatic components of 2 rings or more, (II) 1-ring aromatic components having a hydrocarbon group of two or more carbons, and (III) 1-ring aromatic components having a naphthenic ring; and
    d) introducing the (c)(i) into a transalkylation step in the presence of a transalkylation catalyst to produce a transalkylated product,
        separating the transalkylated product into a first aromatics stream comprising benzene and xylenes and a second aromatics stream comprising 11 or more carbon atoms, and
        recirculating the second aromatics stream to step (b);
    e) separating the (c)(ii) to recover a stream comprising at least a portion of $C_{2-4}$ olefins;
    f) recirculating the (c)(iii) to step (a) or step (b).

2. The method of claim 1, wherein the hydroprocessing catalyst comprises at least one carrier selected from alumina and silica, and at least one metal selected from group 6, group 9 metals and group 10 metals.

3. The method of claim 2, wherein the at least one metal is selected from cobalt, molybdenum, nickel and tungsten.

4. The method of claim 1, wherein the oil fraction comprises 5 wt % or more of aromatics.

5. The method of claim 1, wherein the oil fraction is selected from raw pyrolysis gasoline (RPG), heavy raw pyrolysis gasoline (heavy RPG), treated pyrolysis gasoline (TPG), reformate, heavy aromatics, kerosene, jet oil, atmospheric gas oil, FCC gasoline, light cracked naphtha, heavy cracked naphtha, FCC decanted oil, vacuum gas oil, coker gas oil, coker diesel, coker naphtha, heavy and reduced petroleum crude oil, petroleum atmospheric distillation bottom oil, petroleum vacuum distillation bottom oil, pitch, asphalt, bitumen, tar sand oil, shale oil, liquid products derived from coal liquefaction processes, heavy hydrocarbon residue0, and combinations thereof.

6. The method of claim 1, wherein the cracking catalyst is a spherical catalyst comprising an amorphous solid acid including silica and alumina or a spherical catalyst comprising a crystalline zeolite molecular sieve having a silica/alumina molar ratio of 300 or less and a pore size of 4-10 Angstroms.

7. The method of claim 6, wherein the cracking catalyst is prepared by mixing 10-95 wt % of at least one zeolite molecular sieve selected from the group consisting of faujasite (FAU), mordenite (MOR) and zeolite beta (BEA) with 5-90 wt % of an inorganic binder selected from alumina and clay and then spray drying the mixture to have a particle size of 10-300 μm.

8. The method of claim 1, further comprising separating and recovering naphthalenes from the residual oil fraction.

9. The method of claim 1, further comprising separating the $C_{2-4}$ olefins into a ethylene stream, a propylene stream and a butylene stream.

10. The method of claim 1, further comprising separating xylenes from the transalkylated product and further separating said xylenes into a stream comprising para-xylene and a stream comprising ortho- and meta-xylenes.

11. The method of claim 9, further comprising separating xylenes from the transalkylated product and further separating into a stream comprising para-xylene and a stream comprising ortho- and meta-xylenes.

12. The method of claim 10, further comprising isomerizing the the stream comprising ortho- and meta-xylenes and recirculating the isomerized xylenes to the transalkylation step.

13. The method of claim 11, further comprising isomerizing the the stream comprising ortho- and meta-xylenes and recirculating the isomerized xylenes to the transalkylation step.

* * * * *